United States Patent [19]

Haupt

[11] Patent Number: 5,037,443
[45] Date of Patent: Aug. 6, 1991

[54] ARTIFICIAL JOINTLESS FOOT

[75] Inventor: Werner Haupt, Duderstadt, Fed. Rep. of Germany

[73] Assignee: Otto Bock Orthopaedische Industrie Besitz - und Verwaltungs - Kommanditgesellschaft Industriestrasse, Duderstadt, Fed. Rep. of Germany

[21] Appl. No.: 54,446

[22] Filed: May 27, 1987

[30] Foreign Application Priority Data

Dec. 29, 1986 [DE] Fed. Rep. of Germany ....... 3644612

[51] Int. Cl.$^5$ .............................................. A61F 2/66
[52] U.S. Cl. ......................................... 623/53; 623/55
[58] Field of Search .................................... 623/53–55, 623/49

[56] References Cited

U.S. PATENT DOCUMENTS

| 757,287 | 4/1904 | Duggan | 623/55 |
| 817,340 | 4/1906 | Rosenkranz | 623/49 |
| 4,007,497 | 2/1977 | Haupt | 623/55 |
| 4,506,395 | 3/1985 | Haupt | 623/53 |
| 4,652,266 | 3/1987 | Truesdell | 623/55 |

FOREIGN PATENT DOCUMENTS 326131 9/1920 Fed. Rep. of Germany ........ 623/55

Primary Examiner—Randall L. Green
Assistant Examiner—David H. Willse
Attorney, Agent, or Firm—Foley & Lardner

[57] ABSTRACT

An artificial jointless foot comprises a wooden core forming an upper connecting surface with an elastic synthetic material connected to the wooden core for forming the foot shape and guaranteeing a flexible rolling action. The wooden core forms, on the connecting surface, a dorsal stop for an adaptor connectable to the stop. Deformation of the connecting surface in the region of the dorsal stop is prevented, even when wood not resistant to such load is used for the wooden core. The wooden core has, in the region of the dorsal stop, a recess open at the top and filled with a duroplastic cast resin, the surface of which is in line with the connecting surface.

12 Claims, 1 Drawing Sheet

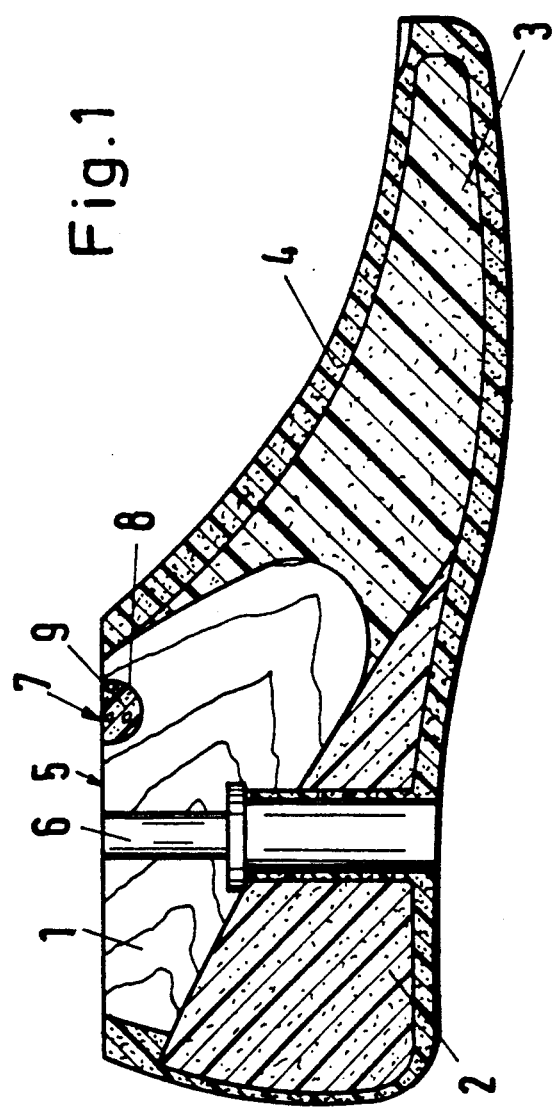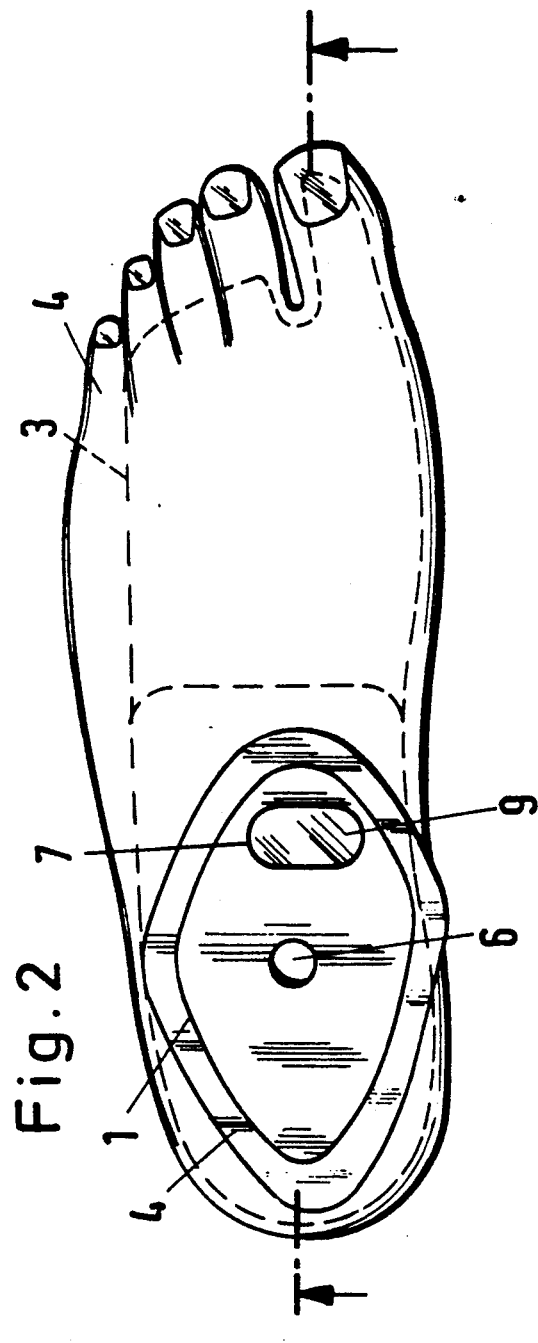

ARTIFICIAL JOINTLESS FOOT

BACKGROUND OF THE INVENTION

The present invention relates to an artificial jointless foot having an incompressible wooden core forming an upper connecting surface, and with elastic synthetic materials connected to the core for forming the foot shape and ensuring a flexible rolling action. The wooden core forms, on the connecting surface, a dorsal stop for an adaptor connectable to the core and tiltable relative to the core.

Jointless feet have been known for a long time and are in frequent use. By means of a skillful arrangement of flexible materials on the wooden core, jointless feet can be designed so that they are in no way inferior to and can even surpass a jointed foot in terms of walking ease.

The wooden core of jointless feet of this type should be produced from wood which is as light as possible. Light and inexpensive wood can perform all the functions of the core of such a jointless foot. The disadvantage associated with such a soft wood is that pronounced wear occurs on its connecting surface in the region of the dorsal stop. This pronounced wear arises because a metal adaptor connected to the foot exerts a load on the surface during each rolling action. During rolling, the adaptor resting on the connecting surface of the wooden core presses with its front edge on this connecting surface. When light wood is used, the connecting surface can quickly become deformed at the location of the dorsal stop. As a result of the play developed, the strength of the connection to the adaptor is no longer guaranteed and undesirable movements of the foot can occur. Furthermore, the screw connection of the adaptor can break resulting in the entire foot prosthesis becoming useless and capable of causing an accident.

This high probability of damage resulted in the use of expensive hard wood to solve the problem, but the use of hard wood increased the weight of the foot prosthesis substantially.

Attempts have already been made to avoid the use of expensive heavy wood by reinforcing the connecting surface of the light wooden core in the region of the dorsal stop. However, an attached metal plate reinforcement can cause an undesirable sliding movement of the adaptor on the connecting surface. Attempts have also been made to replace the surface of the wooden core by a hard-wood insert at the location of the dorsal stop. It was shown, however, that, because of the high load, it is not possible to make a stable connection between the hard-wood insert and the wooden core by means of adhesive bonding or the like.

SUMMARY OF THE INVENTION

It is therefore an object of the present invention to provide an artificial jointless foot having a stop member for preventing wear.

It is also an object of the present invention to provide an artificial jointless foot having a core made from light wood which is resistant to wear.

It is a further object of the present invention to provide a resin stop which can be inserted into a wooden core for prevention of wear.

It is another object of the present invention to provide an artificial jointless foot that can withstand an extreme load exerted by an artificial leg.

Still another object of the present invention is to provide an artificial jointless foot which ensures a flexible rolling action.

Another object of the present invention is to provide an artificial jointless foot of the type mentioned in the introduction, so that wear of the wooden core in the region of the dorsal stop is effectively prevented, even when relatively soft and light wood is used for the wooden core.

In accordance with one aspect of the present invention, these objects are achieved by an artificial jointless foot comprising: a wooden core having an upper connecting surface and means comprising a resin and disposed in a dorsal stop region on the connecting surface for preventing the wear of the upper connecting surface caused by the force exerted by an artificial leg adaptor which is in communication with the foot during the usage thereof.

There has also been provided an artificial foot, wherein the wear preventing means is disposed within a recess of the upper connecting surface, the recess being open at the top and filled with the wear preventing means such that the surface of the wear preventing means forms a substantially planar surface with the upper connecting surface.

In accordance with another aspect of the present invention, these objects are achieved by an artificial foot dorsal stop comprising: a duroplastic cast resin disposed in a wooden core of the foot and being communicatable with an artificial leg adaptor so as to prevent the wear of the core caused by the force exerted by the adaptor during the usage of the foot.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

An illustrative embodiment of the invention is described in further detail below and is represented schematically in the drawing, in which:

FIG. 1 shows a front view of a longitudinal section through an artificial jointless foot taken along the line I—I in FIG. 2, and FIG. 2 shows a top plan view of the foot shown in FIG. 1.

DETAILED DESCRIPTION OF THE PREFERRED EMBODIMENTS

The present invention comprises a wooden core having, in the region of the dorsal stop, a recess open at the top and filled with a duroplastic cast resin, the surface of which is in line with the connecting surface.

In a preferred embodiment, the duroplastic cast resin is provided with a filler.

In a surprisingly simple way, the wear of the wooden core in the region of the dorsal stop can be prevented by filling the recess in the wooden core with duroplastic cast resin. The duroplastic cast resin makes a secure, firm connection to the wooden core and can be introduced in a simple way so that the resin surface is exactly in line with the connecting surface. If appropriate, the connecting surface as a whole can subsequently be machined for aligning the surface.

Tests have shown that, despite an extreme load exerted on the surface of the cast resin, the resin is anchored firmly in the wooden core and there are no signs of wear.

As a result of the simple inexpensive measure described above, the artificial jointless foot according to the present invention can be constructed with an inexpensive light wooden core.

A filled cast resin is preferably used as a duroplastic cast resin, with slate flour, glass, sand or the like being appropriate as a filler. The filler makes it possible not only to reduce the cost of the cast resin used, but also to lessen the exothermic reaction normally occurring during the hardening of the cast resin and thus increase the compressive strength of the resin.

A two-component cast resin, one component acting as a hardener, is normally used as a hardening cast resin, but it is also possible to use a cast resin which hardens under the effect of ultraviolet radiation.

The foot of the present invention, illustrated in the drawing, comprises a wooden core 1, a heel wedge 2 located in the heel region of the foot, an inner foot 3 adjoining the front side of the wooden core 1 and the heel wedge 2, and an enveloping layer 4 constituting the skin. The core 1 forms an upper connecting surface 5, onto which an adaptor for connection to an artificial leg is attached. To fasten the adaptor, there is a bore 6 which extends into the wooden core 1 perpendicularly to the connecting surface 5 and which widens in the manner of a step at the lower edge of the wooden core 1. The bore 6 receives the shank and head of a fastening screw.

The front edge of the adaptor (not shown) rests on the connecting surface 5 at a location where a dorsal stop 7 is formed. In the region of the dorsal stop 7, the wooden core 1 is hollowed out on the surface in the form of an oblong hole and forms a recess 8 open at the top.

The recess 8 is filled with a duroplastic cast resin 9 mixed with slate flour, glass dust or sand as a filler. The surface of the cast resin 9 is in line with the connecting surface 5, so that a common planar surface is obtained.

The cast resin penetrates into the wood pores of the recess 8 and is firmly connected to the wooden core 1.

The surface of the cast resin 9 is not damaged by the load exerted by the adaptor. The strength of the connection between the cast resin 9 and the wooden core 1 is not impaired by the load.

The dorsal stop 7 is therefore suitable for any load exerted by the adaptor, irrespective of the properties of the wooden core 1.

What is claimed is:

1. An artificial jointless foot comprising: (a) a wooden core that comprises (i) an underside and (ii) an upper connecting surface that comprises a dorsal stop region, (b) a heel wedge connected to said underside of said core in a heel region of said foot, (c) an inner foot member adjoining a front surface of said core, said inner foot member extending into a toe region of said foot, and (d) a skin-forming layer surrounding said core, heel wedge and inner foot member, with the exception of said upper connecting surface of said core, wherein said core comprises means for preventing wear of said surface caused by a force exerted by an artificial leg adaptor that is in contact with said foot during usage thereof, wherein said wear preventing means comprises a hard and wear resistant resin insert disposed within said wooden core in the dorsal stop region.

2. An artificial foot as claimed in claim 1, wherein said wear preventing means is disposed within a recess of said core, said recess being open at the top and filled with said wear preventing means.

3. An artificial foot as claimed in claim 1, wherein said inner foot member is comprised of at least one elastic synthetic material for forming the foot shape and ensuring a flexible rolling action of said foot.

4. An artificial foot as claimed in claim 1, wherein said resin comprises a duroplastic cast resin.

5. An artificial foot as claimed in claim 1, wherein said resin further comprises a filler for hardening said resin.

6. An artificial foot as claimed in claim 5, wherein said filler comprises slate flour, glass or sand.

7. An artificial foot as claimed in claim 1, wherein said resin is one that hardens under the effect of ultraviolet radiation.

8. An artificial foot as claimed in claim 1, further comprising a bore extending into said wooden core perpendicular to said connecting surface, said bore being wider in the manner of a step at the lower edge of said core, for receiving the artificial leg adaptor.

9. An artificial foot as claimed in claim 2, wherein said recess is in the form of an oblong shaped hole.

10. An artificial foot as claimed in claim 1, wherein said resin is a two-component cast resin, one component of which is a hardener.

11. An artificial foot as claimed in claim 1, wherein said core comprises a relatively soft and light wood.

12. An artificial foot as claimed in claim 2, wherein said resin comprises a curable resin which has been filled into said recess in an uncured state and thereafter has been cured so as to be hard and wear resistant.

* * * * *